(12) United States Patent
De Nanteuil et al.

(10) Patent No.: US 7,981,920 B2
(45) Date of Patent: Jul. 19, 2011

(54) ADDITION SALTS OF ANGIOTENSIN-CONVERTING ENZYME INHIBITORS WITH NO DONOR ACIDS, A PROCESS FOR THEIR PREPARATION AND PHARMACEUTICAL COMPOSITIONS CONTAINING THEM

(75) Inventors: Guillaume De Nanteuil, Suresnes (FR); Bernard Portevin, Fay aux Loges (FR); Philippe Gloanec, Mary le Roi (FR); Jean-Gilles Parmentier, Issy les Moulineaux (FR); Alain Benoist, Franconville (FR); Tony Verbeuren, Vernouillet (FR); Alain Rupin, Savonnieres (FR); Christine Courchay, Igny (FR); Serge Simonet, Conflans Sainte Honorine (FR)

(73) Assignee: Les Laboratoires Servier, Suresnes Cedex (FR)

( * ) Notice: Subject to any disclaimer, the term of this patent is extended or adjusted under 35 U.S.C. 154(b) by 129 days.

(21) Appl. No.: 12/283,928

(22) Filed: Sep. 17, 2008

(65) Prior Publication Data

US 2009/0082393 A1    Mar. 26, 2009

(30) Foreign Application Priority Data

Sep. 21, 2007  (FR) ..................................... 07 06629

(51) Int. Cl.
*A61K 31/404* (2006.01)
*C07D 209/12* (2006.01)
(52) U.S. Cl. ........................................ 514/412; 548/452
(58) Field of Classification Search .................... 548/452
See application file for complete search history.

(56) References Cited

FOREIGN PATENT DOCUMENTS

| EP | 0575754 | 12/1993 |
|---|---|---|
| WO | WO 00/12110 | 3/2000 |
| WO | WO 2004/050084 | 6/2004 |
| WO | WO 2006/078995 | 7/2006 |
| WO | WO 2006/102071 | 9/2006 |
| WO | WO 2006102071 A1 * | 9/2006 |
| WO | WO 2007/059311 | 5/2007 |
| WO | WO 2007/060112 | 5/2007 |

OTHER PUBLICATIONS

Cancer and Metastasis Reviews (1998), 17(10, 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Pokrovskii, M.A., et al."Method for correcting endothelial dysfunction" Database CA, Chemical Abstract Service, Database accession No. 2006:21218242.
Persson, K., et al., "Nitric oxide donors and angiotensin-converting enzyme inhibitors act in concert to inhibit human angiotensin-converting enzymen activity and platelet aggregation in vitro" European Journal of Pharmacology vol. 406, No. 1, p. 15-23, 2000.
Wang, Peng George, et al., "Nitric oxide donors: Chemical activities and biological application" Chemical Reviews, vol. 102, No. 4, p. 1091-1134, 2002.
Stanisavljevic, Sinisa, et al., "Angiotensin I-converting enzyme inhibitors block protein kinase C.epsilon. by activating bradykinin B1 receptors in human endothelial cells" Journal of Pharmacology and Experimental Therapeutics. vol. 316, No. 3, p. 1153-1158, 2006.
Walter Haefeli, et al., "quinaprilat induces arterial vasodilation mediated by nitric oxide in humans" Database CA, Chemical Abstract Service, Database accession No. 1997:710123.
Francisco Ruiz, et al., "N-acetyl-L-cysteine protentiates depressor response to captopril and enalaprilat in SHRs", Database CA, Chemical Abstract Service, Database accession No. 1995: 263273.
P. Massoudy, et al., "Nitric oxide accounts for postischemic cardioprotection resulting from angiotensin-converting enzymen inhibition: indirect evidence for a radical scavenger effect in isolated guinea pig heart" Database CA, Chemical Abstract Service, Database accession No. 1995:408239.
Giovanni Sorba, et al., "water soluble furoxan derivatives as NO prodrugs" Journal of Medicinal Chemistry, vol. 40, No. 4, p. 463-469, 1997.
French Preliminary Search Report for French Application No. FR 0706629, Jul. 7, 2008.
European Search Report for European Application No. EP 08290885, Nov. 7, 2008.

* cited by examiner

*Primary Examiner* — Shawquia Young
(74) *Attorney, Agent, or Firm* — Hueschen and Sage

(57) ABSTRACT

Compounds of formula (I):

$$(A)_m \cdot (B)_n \quad\quad (I)$$

wherein A represents an angiotensin-converting enzyme inhibitor compound containing at least one salt-forming basic function, B represents a compound containing at least one salt-forming acid function and at least one NO donor group, m represents the number of acid functions of B that have been converted to a salt and n represents the number of basic functions of A that have been converted to a salt,
the bond or bonds between A and B being of the ionic type.
Medicinal products containing the same which are useful in treating cardiovascular pathologies.

7 Claims, No Drawings

ADDITION SALTS OF ANGIOTENSIN-CONVERTING ENZYME INHIBITORS WITH NO DONOR ACIDS, A PROCESS FOR THEIR PREPARATION AND PHARMACEUTICAL COMPOSITIONS CONTAINING THEM

The present invention relates to new addition salts of angiotensin-converting enzyme inhibitors with NO donor acids, to a process for their preparation and to pharmaceutical compositions containing them.

Those compounds may be used in the field of hypertension and cardiovascular disease.

Hypertension brings about an increased risk of vascular accidents, especially at the cerebral and coronary level. It is more and more frequently associated with other pathologies such as atherosclerosis or with metabolic disorders such as obesity, diabetes or renal insufficiency, which appreciably increases the risk of spasms and thromboses.

Since the discovery of its cardiovascular action in 1980, nitrogen monoxide (NO) has been recognised as a vasodilatory and vasoprotective molecule capable of preventing vasospasms, atherosclerosis and thrombosis, that mediator thus offering protection against cardiovascular disease. NO is essentially produced by the endothelium. NO is generally recognised as having vasodilatory, anti-adhesive, anti-thrombotic, anti-inflammatory and anti-oxidant properties.

Inhibitors of angiotensin-converting enzyme (ACE), such as perindopril (Ferrari et al., 2005, Am J Hypertension, 18, 142S-154S), are therapeutic agents the cardiovascular-protecting effects of which are well known; these products reduce arterial pressure, myocardial infarction, cardiac insufficiency, left ventricular dysfunction, stroke and cardiovascular mortality. Those beneficial effects are also observed in diabetic patients with or without atherosclerosis. For perindopril, recent clinical data have demonstrated its anti-atheromatous and anti-inflammatory properties and its beneficial effects on endothelial dysfunction (Ferrari et al., 2005). By blocking the converting enzyme, the ACE inhibitors (1) prevent the formation of angiotensin II, a potent vasoconstrictor that is implicated in cardiovascular disease (Kon and Jabs, 2004, Current Opinion Nephrol Hypertens, 13, 291-297; Unger, 2002, Am J Cardiol, 89, 3A-10A; Ferrari et al., 2005) and (2) protect against the degradation of bradykinin, the beneficial cardiovascular effects of bradykinin (by way of anti-ischaemic effects) being due to the endothelial production of NO (Unger 2002; Ferrari et al., 2005).

It is a well-established fact in a number of pathological conditions, such as atherosclerosis, hypertension, diabetes and others, that the production of NO is reduced or even completely absent (Gewaltig and Kodja, 2002, Cardiovasc Res, 55, 250-260; Russo et al, 2002, Vasc Pharmacol, 38, 259-269). In that condition of endothelial dysfunction, the beneficial effects of the ACE inhibitors combined with inhibition of the degradation of bradykinin will be expressed to a lesser extent. It has been postulated that hybrid products, ACE inhibitors and NO donors, might be beneficial in those various pathological conditions, more specifically in cardiovascular pathologies.

NO donor compounds, such as nitroglycerine, have furthermore been used for a long time to treat angina pectoris and cardiac insufficiency. The beneficial effect of those products is associated with their capacity to form NO (spontaneously or metabolically). Their use has also led to the observation that, in the hypertensive subject, those NO donors cause a substantial reduction in systolic arterial pressure (Nesbitt, 2005, Hypertension, 45, 352-353). Uncontrolled systolic arterial pressure is a significant risk factor for cerebral and cardiac accidents and is often resistant to anti-hypertensive treatments. Indeed, despite the demonstrated anti-hypertensive and vasoprotective effects of products such as ACE inhibitors and other classes of anti-hypertensive products, arterial pressure, especially systolic arterial pressure, remains difficult to control, and the morbidity and mortality rate remains high in hypertensive subjects.

Thus, the addition of NO donor properties to ACE inhibitors such as perindopril appears to be a significant strategy in the fight against cardiovascular disease. Indeed, having NO donor properties would improve the antihypertensive, cardioprotective and vasculoprotective properties, since NO is a vasodilatory, anti-platelet (and thus anti-thrombotic), anti-adhesive and anti-oxidant molecule (Walford et al., 2003, J. Thromb. Haemost., 1, 2112-2118; Gewaltig and Kodja, 2002, Cardiovasc Res, 55, 250-260).

The compounds of the present invention exhibit such a dual pharmacological activity, which confers upon them valuable properties in the field of hypertension and of cardiovascular pathologies.

More specifically, the present invention relates to the salts of formula (I):

$$(A)_m \cdot (B)_n \quad (I)$$

wherein A represents an angiotensin-converting enzyme inhibitor compound containing at least one salt-forming basic function, B represents a compound containing at least one salt-forming acid function and at least one NO donor group, m represents the number of acid functions of B that have been converted to a salt and n represents the number of basic functions of A that have been converted to a salt, the bond or bonds between A and B being of the ionic type.

By a "salt-forming basic function" there is understood a function that is capable of accepting a proton.

As an example of a salt-forming basic function there may be mentioned a primary, secondary or tertiary amine.

By a "salt-forming acid function" there is understood a function that is capable of releasing a proton.

As an example of a salt-forming acid function there may be mentioned a $-CO_2H$, $-SO_3H$ or $P(O)(OH)_2$ group.

By an NO donor group there is understood a group that is capable of donating, releasing and/or transferring nitrogen monoxide or a biologically active form thereof, and/or of stimulating in vivo the endogenous production of nitrogen monoxide or a biologically active form thereof.

Preferably, the angiotensin-converting enzyme inhibitor A belongs to the following formula (II):

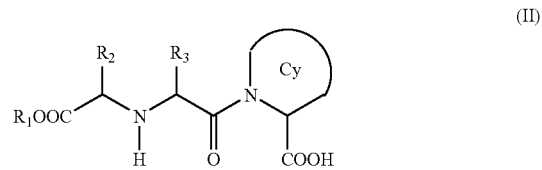

wherein:
- $R_1$ represents a hydrogen atom or a linear or branched $C_1$-$C_6$alkyl group,
- $R_2$ represents a linear or branched $C_1$-$C_6$alkyl group or an aryl-($C_1$-$C_6$)alkyl group in which the alkyl group is linear or branched,
- $R_3$ represents a linear or branched $C_1$-$C_6$alkyl group or an amino-($C_1$-$C_6$)alkyl group in which the alkyl group is linear or branched,

represents a monocyclic or bicyclic nitrogen-containing system having from 3 to 12 carbon atoms and capable of having one or more additional hetero atoms selected from N, O and S, the said system optionally being substituted by one or more groups selected from linear or branched $C_1$-$C_6$alkyl, linear or branched $C_1$-$C_6$alkoxy, oxo, carboxy, aryl, $C_3$-$C_8$cycloalkyl, heteroaryl, carboxy-($C_1$-$C_6$)alkyl in which the alkyl group is linear or branched, and hydroxy, wherein when the nitrogen-containing system is bicyclic, it may be fused, spiro or bridged.

preferably represents a pyrrolidine, perhydroindole, octahydrocyclopenta[b]pyrrole, imidazolidine or tetrahydroisoquinoline ring.

Among the angiotensin-converting enzyme inhibitors A there may be mentioned by way of example enalapril of formula (IIa), enalaprilate of formula (IIb), lisinopril of formula (IIc), perindopril of formula (IId), perindoprilate of formula (IIe), ramipril of formula (IIf), spirapril of formula (IIg), trandolapril of formula (IIh), trandolaprilate of formula (IIi), imidapril of formula (IIj), moexipril of formula (IIk), quinapril of formula (IIm) and ramiprilate of formula (IIn).

(IIa)
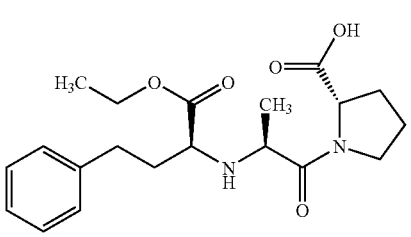

(IIb)
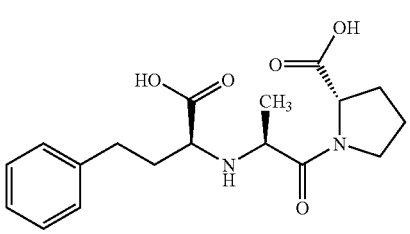

(IIc)
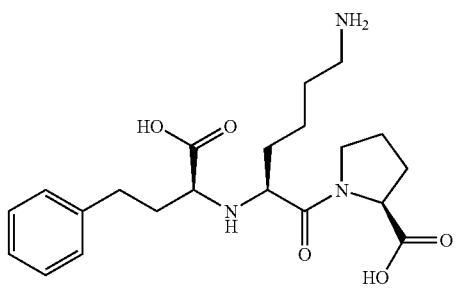

(IId)
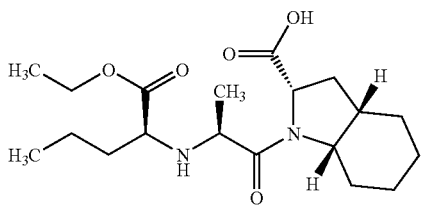

(IIe)
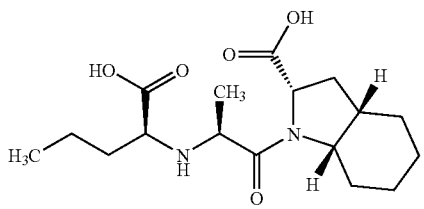

(IIf)
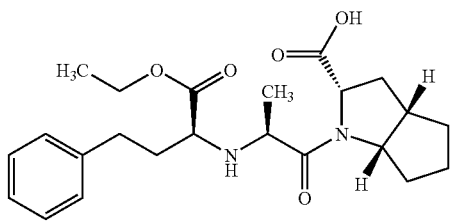

(IIg)
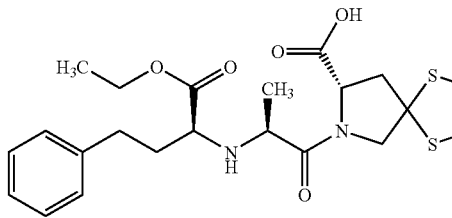

(IIh)
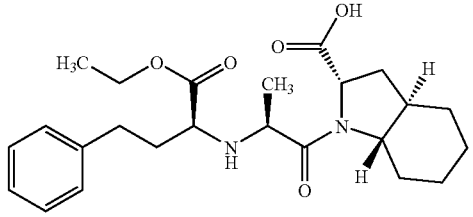

(IIi)
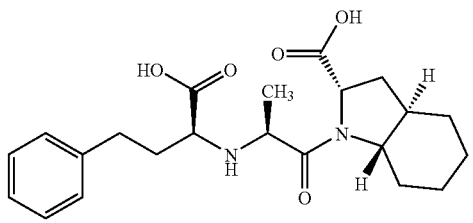

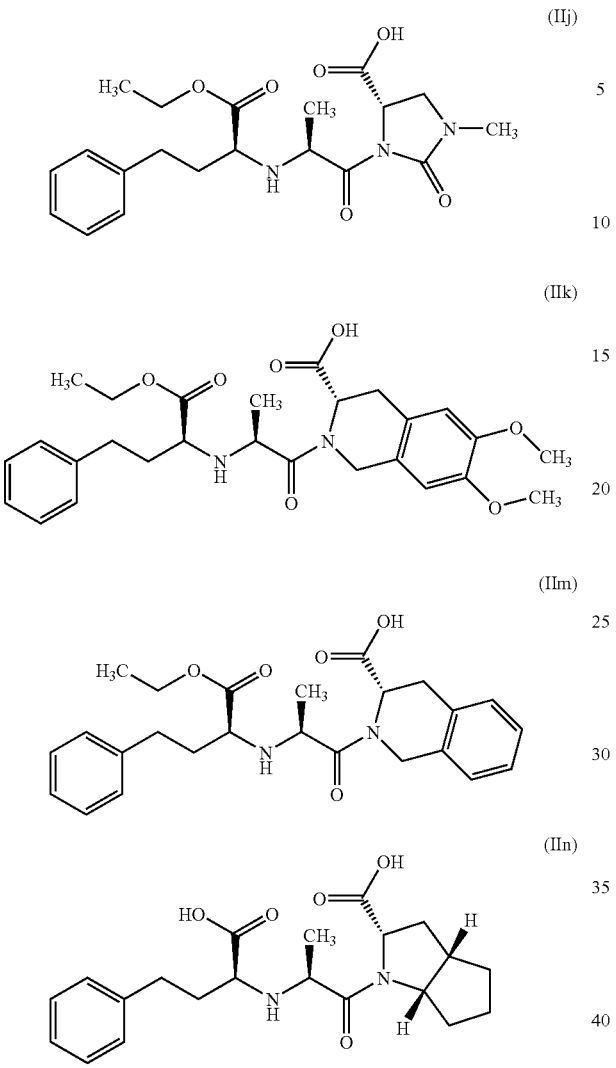
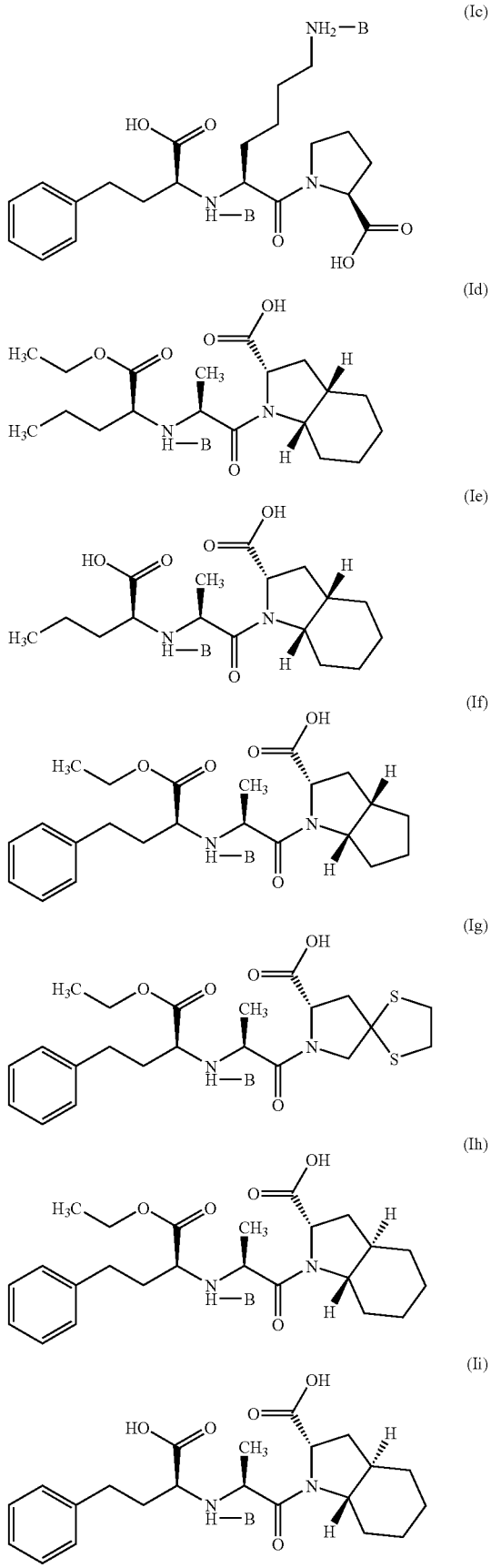
The following compounds are preferred compounds of formula (I):

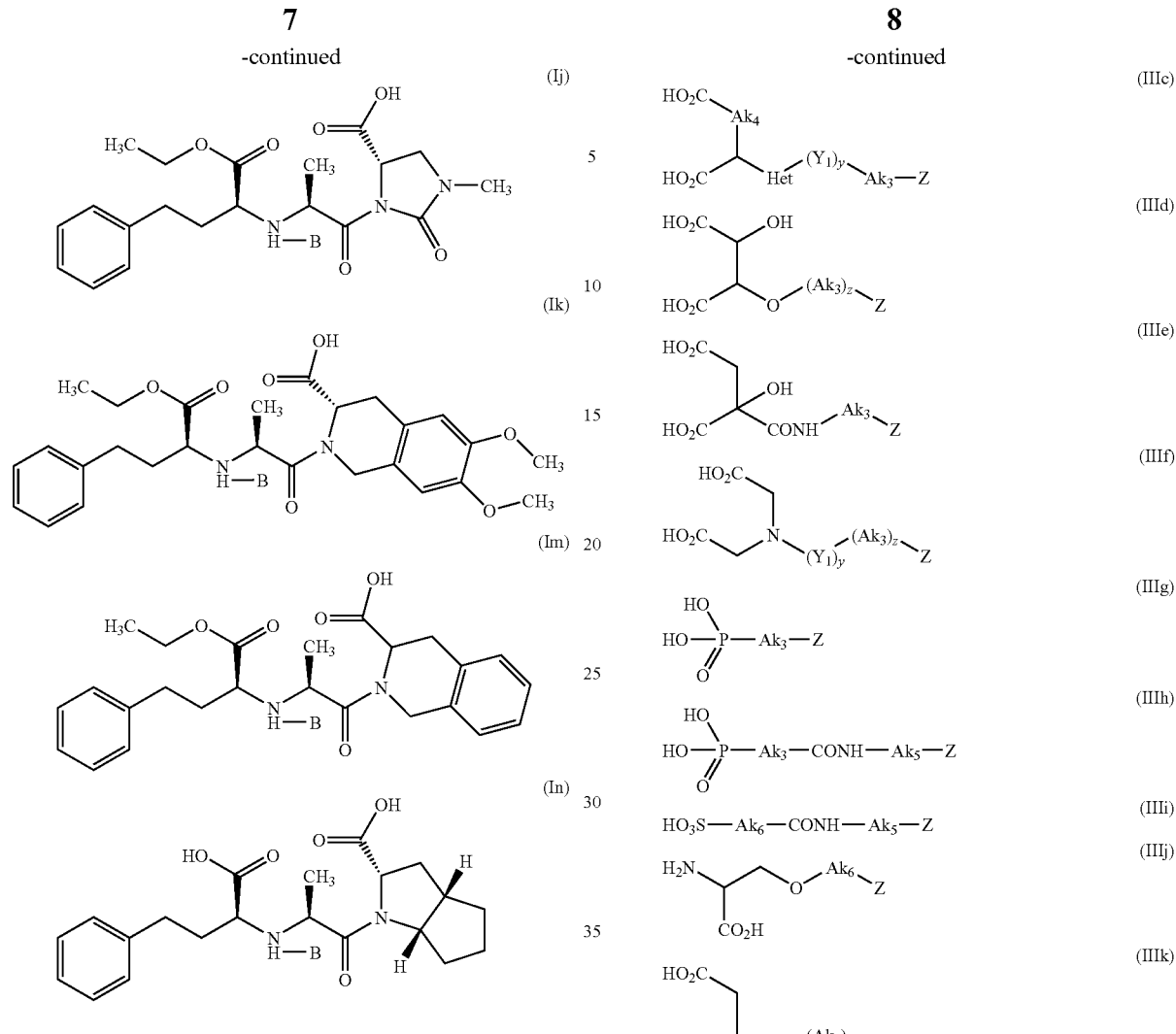

Preferably, compound B belongs to the following formula (III):

$$X\text{-}(Ak_1)_x\text{-}(Y)_y\text{-}(Ak_2)_z\text{-}Z \quad (III)$$

wherein:

X represents a $CO_2H$, $SO_3H$ or $P(O)(OH)_2$ group, $Ak_1$ and $Ak_2$, which may be identical or different, each represents a saturated or unsaturated, linear or branched $C_1$-$C_8$alkylene group in which one or more of the carbon atoms may be replaced by an oxygen, sulphur or nitrogen atom or by an $SO_2$ group, the said alkylene group optionally being substituted by one or more groups selected from $CO_2H$, $SO_3H$, hydroxy and amino, x, y and z, which may be identical or different, each represents 0 or 1, Y represents CO or CONH, Z represents an NO donor group.

Among the compounds of formula (III), the compounds belonging to one of the formulae below may be mentioned:

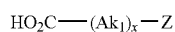 (IIIa)

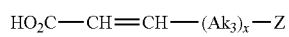 (IIIb)

in which formulae:

$Ak_1$, x, y, z and Z are as defined hereinbefore, $Ak_3$ and $Ak_5$, which may be identical or different, each represents a saturated linear or branched $C_1$-$C_6$alkylene group in which one or more of the carbon atoms may be replaced by an oxygen, sulphur or nitrogen atom or by an $SO_2$ group, $Ak_4$ represents a saturated linear or branched $C_1$-$C_3$alkylene group in which one of the carbon atoms may be replaced by an oxygen, sulphur or nitrogen atom or by an $SO_2$ group, $Ak_6$ represents a saturated linear or branched $C_2$-$C_5$alkylene group in which one of the carbon atoms may be replaced by an oxygen, sulphur or nitrogen atom or by an $SO_2$ group, Het represents O or NH, and $Y_1$ represents a carbonyl group.

Preferably, Z is selected from the following groups:

-continued (Z₃), (Z₄), (Z₅), (Z₆), (Z₇), (Z'₇), (Z₈), (Z'₈), (Z₉), (Z'₉)

in which formulae:

m represents 0 or 1,

R₁ and R₂, which may be identical or different, each represents a linear or branched $C_1$-$C_6$alkyl group, or R₁ and R₂, together with the nitrogen atom carrying them, form a nitrogen-containing heterocycle having from 3 to 7 ring members which is optionally substituted by a linear or branched $C_1$-$C_6$alkyl group, R₃ represents a methyl or aminocarbonyl group, and R₄ and R'₄, which may be identical or different, each represents a hydrogen or halogen atom or a linear or branched $C_1$-$C_6$alkyl, trifluoromethyl or trifluoromethoxy group.

By a nitrogen-containing heterocycle having from 3 to 7 ring members there is understood a saturated monocyclic group having from 3 to 7 ring members that contains one, two or three hetero atoms, one of those hetero atoms being a nitrogen atom and the additional hetero atom or atoms that may be present being selected from the atoms oxygen, nitrogen and sulphur.

The nitrogen-containing heterocycle having from 3 to 7 ring members that is preferred is the pyrrolidinyl group.

Preferred B compounds are as follows:

(B₁), (B₂), (B₃), (B₄), (B₅), (B₆)

(B7)
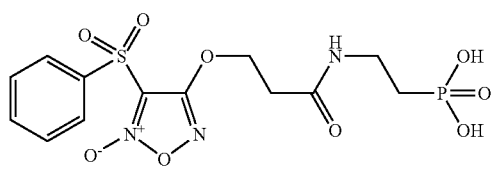
(B8)
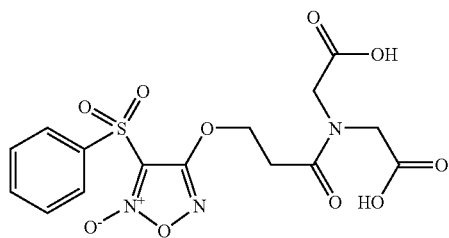
(B9)
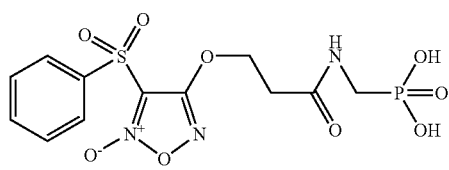
(B10)
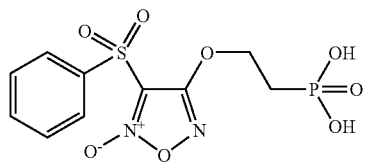
(B11)
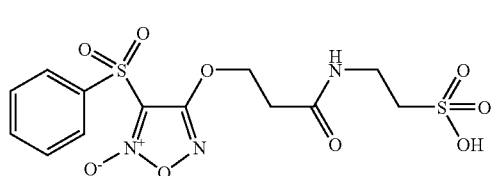
(B12)
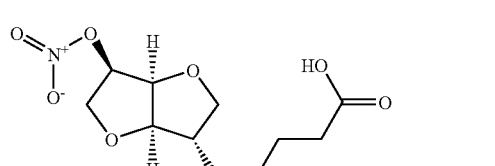
(B13)
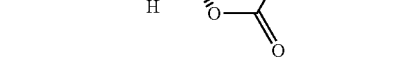
(B14)
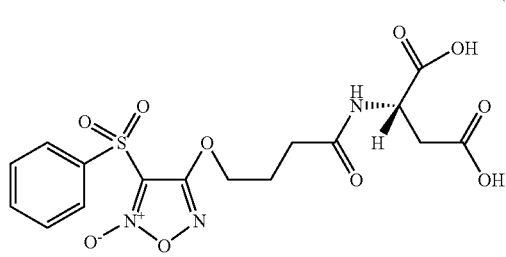
(B15)
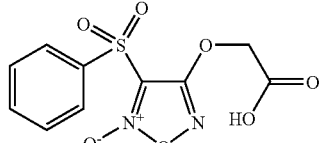
(B16)
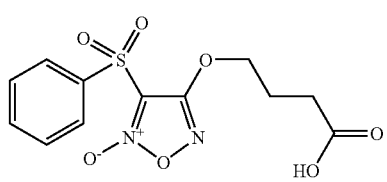
(B17)
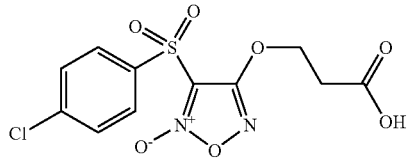
(B18)
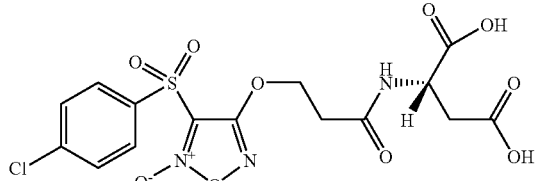
(B19)
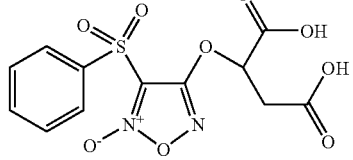
(B20)
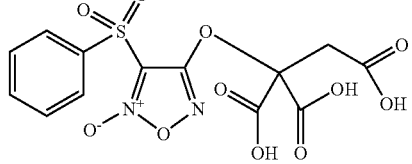
(B21)
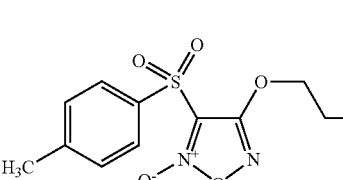
(B22)
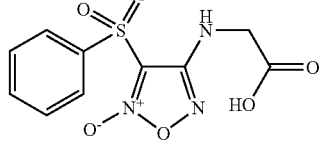

-continued

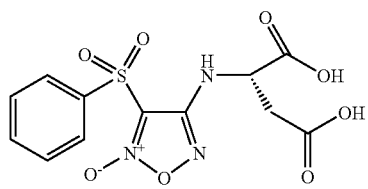
(B23)

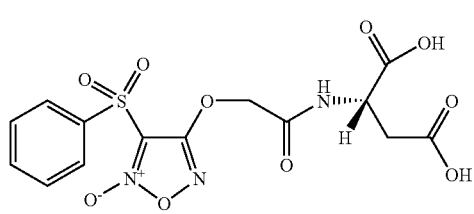
(B24)

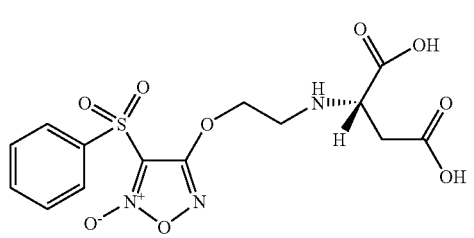
(B25)

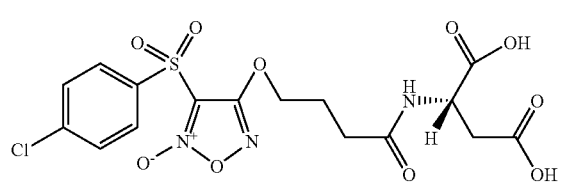
(B26)

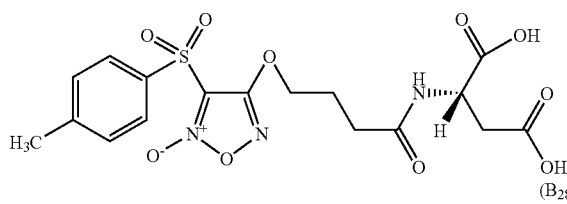
(B27)

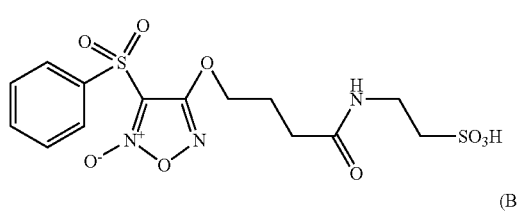
(B28)

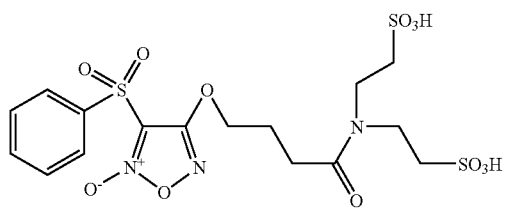
(B29)

Preferred compounds of formula (I) are as follows:

(2S)-2-[(3-{[5-oxido-4-(phenylsulphonyl)-1,2,5-oxadiazol-3-yl]-oxy}-propionyl)-amino]-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S)-2-[(3-{[5-oxido-4-(phenylsulphonyl)-1,2,5-oxadiazol-3-yl]-oxy}-propionyl)-amino]-pentanedioic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

2-[(3-{[5-oxido-4-(phenylsulphonyl)-1,2,5-oxadiazol-3-yl]-oxy}-propionyl)-amino]-ethanesulphonic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-{[(3-{[5-oxido-4-(phenylsulphonyl)-1,2,5-oxadiazol-3-yl]-oxy}-propionyl)-amino]-methyl}-phosphonic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-2,2'-[(3-{[5-oxido-4-(phenylsulphonyl)-1,2,5-oxadiazol-3-yl]-oxy}-propionyl)-imino]-diacetic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-{2-[(3-{[5-oxido-4-(phenylsulphonyl)-1,2,5-oxadiazol-3-yl]-oxy}-propionyl)-amino]-ethyl}-phosphonic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-(2-{[5-oxido-4-(phenylsulphonyl)-1,2,5-oxadiazol-3-yl]-oxy}-ethyl)-phosphonic acid (1:1);

(2S)-2-[(4-{[5-oxido-4-(phenylsulphonyl)-1,2,5-oxadiazol-3-yl]-oxy}-butanoyl)-amino]-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

(2S)-2-{[3-({4-[(4-chlorophenyl)sulphonyl]-5-oxido-1,2,5-oxadiazol-3-yl}oxy)-propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S)-2-{[3-({4-[(4-methylphenyl)sulphonyl]-5-oxido-1,2,5-oxadiazol-3-yl}oxy)-propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S)-2-{[3-({4-[(4-methylphenyl)sulphonyl]-5-oxido-1,2,5-oxadiazol-3-yl}oxy)-butanoyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1).

The present invention relates also to a process for the synthesis of the compounds of formula (I), in which process compound A is reacted with compound B in an amount at least equal to (n/m) equivalents of compound A.

The compounds A of formulae (IIa), (IIb), (IIc), (IId), (IIe), (IIf), (IIg), (IIh), (IIi), (IIj), (IIk), (IIm) and (IIn) are known.

The compounds B can be obtained by conventional reactions of organic chemistry.

By way of example, the compounds $B_1$ and $B_2$ can be obtained from crotonaldehyde, which is converted to 4-methyl-1,2,5-oxadiazole 5-oxide-3-carboxaldehyde by reaction with sodium nitrite in acetic acid. The aldehyde so obtained is then oxidised to yield compound $B_1$ or reacted with a protected triphenylphosphinomethylidenecarboxylic acid compound to yield compound $B_2$ after deprotection.

Compound $B_{12}$ can be obtained by coupling isosorbide mononitrate with succinic anhydride.

The compounds B of formula (III) wherein Z represents the group $Z_9$ or $Z'_9$ can be obtained by reaction between the compound of the following formula:

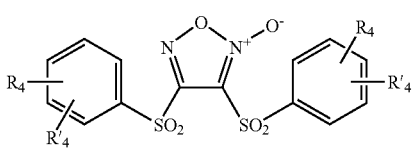

and an alcohol compound X-(Ak$_1$)$_x$-(Y)$_y$-(Ak$_2$)$_z$-OH in which the acid functions are protected, in the presence of a base, followed by deprotection of the acid functions.

Compounds B of formula (III) wherein Z represents the group Z$_9$ or Z'$_9$ are new products for use as synthesis intermediates in the chemical or pharmaceutical industry, especially in the synthesis of the salts of formula (I), and as such form an integral part of the present invention.

In view of their pharmacological properties, the compounds of the present invention are indicated in pathologies that require treatment with an ACE inhibitor and/or with an NO donor, and are of use in the treatment of cardiovascular pathologies such as arterial hypertension (in its various forms) and the vascular and renal sequelae thereof, systolic hypertension, peripheral vascular disease, atherosclerosis, restenosis, cardiac insufficiency, thrombosis and any thromboembolic events, angina pectoris (stable or unstable), cerebral vascular accidents, coronary accidents, myocardial infarction, vascular remodelling, diabetes and the vascular and renal sequelae thereof, complications associated with surgical operations such as cardiovascular surgery, and endothelial dysfunction.

Since NO also has anti-inflammatory and anti-oxidant properties, the compounds of the present invention are of use in the treatment of pathologies involving inflammation and oxidative stress.

The present invention relates also to pharmaceutical compositions comprising as active ingredient a compound of formula (I), in combination with one or more pharmaceutically acceptable, inert, non-toxic, excipients or carriers.

Among the pharmaceutical compositions according to the invention there may be mentioned more especially those that are suitable for oral, parenteral (intravenous, intramuscular or sub-cutaneous), per- or trans-cutaneous, nasal, rectal, perlingual, ocular or respiratory administration, and especially tablets or dragées, sublingual tablets, hard gelatin capsules, capsules, suppositories, creams, ointments, dermal gels, injectable or drinkable preparations, aerosols, eye drops or nose drops etc. . . .

In addition to the compound of formula (I), the pharmaceutical compositions according to the invention contain one or more excipients or carriers, such as diluents, lubricants, binders, disintegrants, absorbents, colorants or sweeteners.

By way of example of excipients or carriers there may be mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: aluminium and magnesium silicate, starch, gelatin, tragacanth, methylcellulose, sodium carboxymethylcellulose and polyvinylpyrrolidone,
- as disintegrants: agar, alginic acid and its sodium salt, effervescent mixtures.

The percentage of active ingredient of formula (I) in the pharmaceutical composition is preferably from 5% to 50% by weight.

The useful dosage varies according to the age and weight of the patient, the administration route, the nature and severity of the disorder and the administration of any associated treatments and ranges from 0.5 mg to 500 mg in one or more administrations per day.

The following Examples illustrate the present invention. The structures of the compounds described in the Examples were determined according to the usual spectrophotometric techniques (infrared, nuclear magnetic resonance, mass spectrometry).

Abbreviations:

| | |
|---|---|
| DCC | N,N'-dicyclohexylcarbodiimide |
| DIEA | N,N-diisopropylethylamine |
| DMAP | 4-dimethylaminopyridine |
| DMF | dimethylformamide |
| EDCI | 1-(3-dimethylaminopropyl)-3-ethylcarbodiimide (hydrochloride) |
| HOBT | 1-hydroxybenzotriazole |
| THF | tetrahydrofuran |
| TFA | trifluoroacetic acid |

EXAMPLE 1

(2S)-2-[(3-{[5-Oxido-4-(phenylsulphonyl)-1,2,5-oxadiazol-3-yl]-oxy}-propionyl)-amino]-succinic Acid-(2S,3aS,7aS)-1-[(2S)-2-{[(1S)-1-(ethoxycarbonyl)-butyl]-amino}-propionyl]-octahydro-1H-indole-2-carboxylic Acid (1:1)

Step A: tert-Butyl 3-[(5-oxido-4-(phenylsulphonyl)-1,2,5-oxadiazol-3-yl)-oxy]-propionate Aqueous 50% NaOH solution (6.4 g-80 mmol) is added in the course of 15 minutes to a solution, cooled to 15° C., of 3,4-bis(phenylsulphonyl)-1,2,5-oxadiazole 2-oxide (16 g-44 mmol) and tert-butyl 3-hydroxypropionate (10 g-68 mmol) in 200 ml of anhydrous THF. After stirring for 2 hours, the solvent is removed in vacuo and the residue is taken up in 100 ml of water and 100 ml of ethyl acetate. The organic phase is decanted off, washed with saturated NaCl solution, dried with sodium sulphate and evaporated.

The remaining oil is purified by flash chromatography using as eluant a (98/2) dichloromethane/ethyl acetate mixture to yield the expected product.

Step B: 3-[(5-Oxido-4-(phenylsulphonyl)-1,2,5-oxadiazol-3-yl)-oxy]-propionic acid (Compound B$_4$)

14 g of the compound obtained in Step A dissolved in 100 ml of dichloromethane are placed under argon, 10 ml of TFA are added, and then stirring is carried out for 6 hours at ambient temperature.

The solvents are removed in vacuo. The residue is crystallised in diisopropyl ether to yield the expected product.

Melting point: 138° C.

Step C: Di-tert-butyl (2S)-2-[(3-{[5-oxido-4-(phenylsulphonyl)-1,2,5-oxadiazol-3-yl]-oxy}-propionyl)-amino]-succinate A solution of the compound obtained in the above Step (2.7 g-8 mmol), di-tert-butyl L-aspartate hydrochloride (2.25 g-8 mmol), EDCI (1.62 g-8 mmol), DIEA (1.32 g-8 mmol) and HOBT (1.1 g-8 mmol) in 100 ml of anhydrous DMF is stirred for 72 hours at ambient temperature under argon. The DMF is removed by distillation and then the residue is taken up in 100 ml of water and 100 ml of ethyl acetate. The organic phase is then washed with 5% NaHCO₃ solution, dried over Na₂SO₄ and then evaporated to dryness. The crude reaction product is purified by flash chromatography using as eluant a (90:10) dichloromethane/ethyl acetate mixture.

Step D: (2S)-2-[(3-{[5-Oxido-4-(phenylsulphonyl)-1,2,5-oxadiazol-3-yl]-oxy}-propionyl)-amino]-succinic acid (Compound B₅)

A solution of the compound obtained in the above Step (4 g-7.3 mmol) in 100 ml of dichloromethane and 15 ml of TFA is stirred for 6 hours under argon. The solvents are distilled off to dryness. The residue is triturated in diisopropyl ether for 2 hours until crystallisation occurs. Filter off with suction, dry.
Melting point: 130-131° C.

Step E: (2S)-2-[(3-{[5-Oxido-4-(phenylsulphonyl)-1,2,5-oxadiazol-3-yl]-oxy}-propionyl)-amino]-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

A solution of perindopril or (2S,3aS,7aS)-1-[(2S)-2-{[(1S)-1-(ethoxycarbonyl)-butyl]-amino}-propionyl]-octahydro-1H-indole-2-carboxylic acid (368 g-1 mmol) and of the compound obtained in the above Step (429 g-1 mmol) in 50 ml of water and 50 ml of acetonitrile is prepared. Filter through Whatman filter and lyophilise.
Elemental microanalysis:

|  | % C | % H | % N | % S |
|---|---|---|---|---|
| Calculated | 51.19 | 5.94 | 8.78 | 4.02 |
| Found | 51.49 | 5.79 | 8.80 | 3.70 |

EXAMPLE 2

(2S,3aS,7aS)-1-[(2S)-2-{[(1S)-1-(Ethoxycarbonyl)-butyl]-amino}-propionyl]-octahydro-1H-indole-2-carboxylic acid-4-methyl-1,2,5-oxadiazole-3-carboxylic acid 5-oxide (1:1)

Step A: 4-Methyl-1,2,5-oxadiazole 5-oxide-3-carboxaldehyde

A solution of crotonaldehyde (100 g-1.42 mol) in 200 ml of acetic acid is cooled to 0-5° C. and added in the course of 3 hours 30 minutes to a solution of sodium nitrite (340 g-4.2 mol) in 400 ml of water. After stirring for 1 hour, 150 ml of water are added and extraction is carried out 6 times with 100 ml of CH₂Cl₂ each time.

The combined organic phases are washed with 100 ml of water, dried over Na₂SO₄ and evaporated to dryness.

The residue is purified by flash chromatography using dichloromethane as eluant.
Melting point: 62° C.

Step B: 4-Methyl-1,2,5-oxadiazole 5-oxide-3-carboxylic acid (Compound B₁)

14.2 g of KMnO₄ (90 mmol) are added in portions in the course of 1 hour 30 minutes, at a temperature maintained at 20° C., to a solution of 7 g of the compound obtained in Step A in 400 ml of water. 100 ml of 1M NaOH are then added and filtration through 200 g of Celite is carried out. The filtrate is then acidified with 100 ml of 1M HCl and concentrated to a volume of 100 ml using a rotary evaporator. Following extraction 8 times with 100 ml of dichloromethane each time, the organic fractions are dried over Na₂SO₄ and then evaporated to yield the expected compound.
Melting point: 92° C.

Step C: (2S,3aS,7aS)-1-[(2S)-2-{[(1S)-1-(Ethoxycarbonyl)-butyl]-amino}-propionyl]-octahydro-1H-indole-2-carboxylic acid-4-methyl-1,2,5-oxadiazole-3-carboxylic acid 5-oxide (1:1)

The compound is obtained according to the procedure described in Step E of Example 1, starting from perindopril and the compound obtained in the above Step.
Elemental microanalysis:

|  | % C | % H | % N |
|---|---|---|---|
| Calculated | 53.90 | 7.08 | 10.93 |
| Found | 54.10 | 7.07 | 11.28 |

EXAMPLE 3

(2R,3R)-2-Hydroxy-3-{[5-oxido-4-(phenylsulphonyl)-1,2,5-oxadiazol-3-yl]-oxy}-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: Di-tert-butyl (2R,3R)-2-hydroxy-3-{[5-oxido-4-(phenylsulphonyl)-1,2,5-oxadiazol-3-yl]-oxy}-succinate 50% NaOH solution (1.2 g-30 mmol) is added in the course of ½ hour to a solution of 3,4-bis(phenylsulphonyl)-1,2,5-oxadiazole 2-oxide (7 g-19 mmol) and di-tert-butyl tartrate (5 g-19 mmol) in 100 ml of anhydrous THF. After stirring for 5 hours, the solvent is evaporated off to dryness and the residue is taken up in water and ethyl acetate. The organic fraction is dried with Na₂SO₄ and evaporated to dryness and subsequently purified by flash chromatography, using a (98:2) dichloromethane/ethanol mixture as eluant, to yield the expected product in the form of a colourless oil.

Step B: (2R,3R)-2-Hydroxy-3-{[5-oxido-4-(phenylsulphonyl)-1,2,5-oxadiazol-3-yl]-oxy}-succinic acid (Compound B₃)

The compound obtained in the above Step is stirred for 4 hours in 50 ml of dichloromethane and 10 ml of TFA.
The solvents are removed in vacuo and the residue is crystallised in diisopropyl ether.
Melting point: 198-200° C.

Step C: (2R,3R)-2-Hydroxy-3-{[5-oxido-4-(phenylsulphonyl)-1,2,5-oxadiazol-3-yl]-oxy}-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Elemental microanalysis:

|  | % C | % H | % N | % S |
|---|---|---|---|---|
| Calculated | 50.13 | 5.70 | 7.54 | 4.32 |
| Found | 49.68 | 5.30 | 7.74 | 4.17 |

EXAMPLE 4

(2S)-2-[(3-{[5-Oxido-4-(phenylsulphonyl)-1,2,5-oxadiazol-3-yl]-oxy}-propionyl)-amino]-pentanedioic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: Di-tert-butyl (2S)-2-[(3-{[5-oxido-4-(phenylsulphonyl)-1,2,5-oxadiazol-3-yl]-oxy}-propionyl)-amino]-pentanedioate A solution prepared from the compound B4 obtained in Step B of Example 1 (2.5 g-8 mmol), di-tert-butyl hydrochloride L-glutamate (2.36 g-8 mmol), EDCI (1.62 g-8 mmol), DIEA (1.32 ml-8 mmol) and HOBT (1.1 g-8 mmol) in 100 ml of anhydrous DMF is stirred for 72 hours at ambient temperature. The DMF is removed by distillation and then the residue is taken up in 100 ml of water and 100 ml of ethyl acetate. The organic phase is washed with 5% $NaHCO_3$ solution and then with water, dried over $Na_2SO_4$ and evaporated to dryness. Purification by flash chromatography is carried out using a (90:10) dichloromethane/ethyl acetate mixture as eluant to yield the expected product in the form of a colourless oil.

Step B: (2S)-2-[(3-{[5-Oxido-4-(phenylsulphonyl)-1,2,5-oxadiazol-3-yl]-oxy}-propionyl)-amino]-pentanedioic acid (Compound $B_6$)

A solution of the compound obtained in Step A (3 g-5.5 mmol) in 100 ml of dichloromethane and 15 ml of TFA is stirred for 6 hours under argon. The solvents are distilled off in vacuo. The residue is triturated in diisopropyl ether, filtered off with suction and then dried in vacuo to yield the expected product in the form of white crystals.
Melting point: 157-158° C.

Step C: (2S)-2-[(3-{[5-Oxido-4-(phenylsulphonyl)-1,2,5-oxadiazol-3-yl]-oxy}-propionyl)-amino]-pentanedioic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N | % S |
|---|---|---|---|---|
| Calculated | 51.78 | 6.08 | 8.63 | 3.95 |
| Found | 51.21 | 5.93 | 8.69 | 3.68 |

EXAMPLE 5

(2E)-3-(4-Methyl-5-oxido-1,2,5-oxadiazol-3-yl)-acrylic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: tert-Butyl (2E)-3-(4-methyl-5-oxido-1,2,5-oxadiazol-3-yl)-acrylate

A solution prepared from the compound obtained in Step A of Example 2 (3.9 g-30 mmol) and tert-butyl triphenylphosphinomethylidenecarboxylate (13.1 g-35 mmol) in 100 ml of anhydrous THF is stirred for 1 hour at ambient temperature.
The solvent is removed in vacuo and then the residue is purified by flash chromatography using dichloromethane as eluant to yield the expected product in the form of white crystals.
Melting point: 72-74° C.

Step B: (2E)-3-(4-Methyl-5-oxido-1,2,5-oxadiazol-3-yl)-acrylic acid (Compound $B_2$)

A solution of the compound obtained in the above Step (6.2 g-27 mmol) in 100 ml of dichloromethane and 10 ml of TFA is stirred for 8 hours at ambient temperature. The solvents are then evaporated off in vacuo and the residue is crystallised in diethyl ether and subsequently filtered off with suction and dried to yield the expected product in the form of white crystals.
Melting point: 160° C.

Step C: (2E)-3-(4-Methyl-5-oxido-1,2,5-oxadiazol-3-yl)-acrylic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N |
|---|---|---|---|
| Calculated | 55.75 | 7.11 | 10.40 |
| Found | 55.90 | 7.06 | 10.25 |

EXAMPLE 6

2-[(3-{[5-Oxido-4-(phenylsulphonyl)-1,2,5-oxadiazol-3-yl]-oxy}-propionyl)-amino]-ethanesulphonic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: N-{2-[(3-{[5-Oxido-4-(phenylsulphonyl)-1,2,5-oxadiazol-3-yl]-oxy}-propionyl)-oxy]}-5-norbornene-2,3-dicarboximide A solution of the compound B4 obtained in Step B of Example 1 (2.5 g-5.4 mmol), N-hydroxy-5-norbornene-2,3-dicarboximide (1.03 g-5.4 mmol) and DCC (1.17 g-5.4 mmol) in 100 ml of anhydrous THF is stirred for 20 hours at ambient temperature. The dicyclohexylurea formed is removed by filtration and the THF is removed by distillation in vacuo.

The crude product is taken up in 80 ml of ethyl acetate, filtered again and evaporated to dryness. The activated ester so obtained is used in Step B without being purified.

Step B: 2-[(3-{[5-Oxido-4-(phenylsulphonyl)-1,2,5-oxadiazol-3-yl]-oxy}-propionyl)-amino]-ethanesulphonic acid (Compound $B_{11}$)

A solution of the activated ester obtained in the above Step (2.56 g-5.4 mmol), taurine (0.81 g-6.5 mmol), and NaHCO$_3$ (0.54 g-6.5 mmol) in 80 ml of water is stirred at ambient temperature for 48 hours. The solvents are removed by distillation in vacuo. The residues are taken up in 100 ml of water and 100 ml of ethyl acetate. Following extraction and decanting, the aqueous phase is eluted on a column of DOWEX 50WX8 cation exchange resin. The solvent is evaporated off in vacuo. The residue is purified on an inverse phase preparative HPLC column eluted with a (650:350:1) water-acetonitrile-TFA mixture. The pure fractions are lyophilised.

Step C: 2-[(3-{[5-Oxido-4-(phenylsulphonyl)-1,2,5-oxadiazol-3-yl]-oxy}-propionyl)-amino]-ethanesulphonic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N | % S |
|---|---|---|---|---|
| Calculated | 48.66 | 6.00 | 8.87 | 8.12 |
| Found | 48.32 | 6.32 | 8.66 | 8.08 |

EXAMPLE 7

(2S,3aS,7aS)-1-[(2S)-2-{[(1S)-1-(Ethoxycarbonyl)-butyl]-amino}-propionyl]-octahydro-1H-indole-2-carboxylic acid-{[(3-{[5-oxido-4-(phenylsulphonyl)-1,2,5-oxadiazol-3-yl]-oxy}-propionyl)-amino]-methyl}-phosphonic acid (1:1)

Step A: {[(3-{[5-Oxido-4-(phenylsulphonyl)-1,2,5-oxadiazol-3-yl]-oxy}-propionyl)-amino]-methyl}-phosphonic acid (Compound $B_9$)

A solution prepared from the compound obtained in Step A of Example 6 (2.14 g-4.5 mmol), aminomethylphosphonic acid (0.7 g-6 mmol) and NaHCO$_3$ (1 g-12 mmol) in 50 ml of dioxane and 50 ml of water is stirred for 72 hours at ambient temperature.

The solvents are then evaporated off to dryness and the residue is taken up in 100 ml of water and 100 ml of ethyl acetate and stirred for 1 hour. After decanting, the aqueous phase is purified on a column of DOWEX 50WX8 cation exchange resin. The residue obtained following evaporation of the water is crystallised in acetonitrile, filtered off with suction and then dried in vacuo to yield the expected product.
Melting point: 171-172° C.

Step B: (2S,3aS,7aS)-1-[(2S)-2-{[(1S)-1-(Ethoxycarbonyl)-butyl]-amino}-propionyl]-octahydro-1H-indole-2-carboxylic acid-{[(3-{[5-oxido-4-(phenylsulphonyl)-1,2,5-oxadiazol-3-yl]-oxy}-propionyl)-amino]-methyl}-phosphonic acid (1:1)

The compound is obtained according to the procedure described in Step E of Example 1, starting from perindopril and the compound obtained in the above Step.
Elemental microanalysis:

|  | % C | % H | % N | % S |
|---|---|---|---|---|
| Calculated | 48.00 | 5.98 | 9.03 | 4.13 |
| Found | 47.38 | 6.05 | 9.07 | 3.97 |

EXAMPLE 8

(2S,3aS,7aS)-1-[(2S)-2-{[(1S)-1-(Ethoxycarbonyl)-butyl]-amino}-propionyl]-octahydro-1H-indole-2-carboxylic acid-2,2'-[(3-{[5-oxido-4-(phenylsulphonyl)-1,2,5-oxadiazol-3-yl]-oxy}-propionyl)-imino]-diacetic acid (1:1)

Step A: tert-Butyl 2,2'-[(3-{[5-oxido-4-(phenylsulphonyl)-1,2,5-oxadiazol-3-yl]-oxy}-propionyl)-amino]-diacetate A solution of the compound obtained in Step B of Example 1 (3.5 g-11 mmol), tert-butyl iminodiacetate (2.74 g-11 mmol), HOBT (1.5 g-11 mmol) and EDCI (2.4 g-12 mmol) in 100 ml of anhydrous DMF is stirred at ambient temperature for 72 hours.

The DMF is removed by distillation in vacuo. The residue is taken up in 100 ml of water and 100 ml of ethyl acetate. The organic phase is washed with aqueous 5% NaHCO$_3$ solution, dried over Na$_2$SO$_4$ and evaporated to dryness. The residue is purified by flash chromatography using as eluant a (95:5) dichloromethane-ethyl acetate mixture to yield the expected product in the form of a colourless oil.

Step B: 2,2'-[(3-{[5-Oxido-4-(phenylsulphonyl)-1,2,5-oxadiazol-3-yl]-oxy}-propionyl)-amino]-diacetic acid (Compound $B_8$)

A solution of the compound obtained in the above Step (800 mg-1.5 mmol) in 50 ml of dichloromethane and 5 ml of TFA is stirred for 6 hours at ambient temperature. The solvents are then evaporated off in vacuo. The residue is crystallised in diisopropyl ether, filtered off with suction, and then dried under a pump vacuum to yield the expected product in the form of white crystals.
Melting point: 154° C. (decomposition).

Step C: (2S,3aS,7aS)-1-[(2S)-2-{[(1S)-1-(ethoxycarbonyl)-butyl]-amino}-propionyl]-octahydro-1H-indole-2-carboxylic acid-2,2'-[(3-{[5-oxido-4-(phenylsulphonyl)-1,2,5-oxadiazol-3-yl]-oxy}-propionyl)-imino]-diacetic acid (1:1)

The compound is obtained according to the procedure described in Step E of Example 1, starting from perindopril and the compound obtained in the above Step.

Elemental microanalysis:

|  | % C | % H | % N | % S |
|---|---|---|---|---|
| Calculated | 51.19 | 5.94 | 8.78 | 4.02 |
| Found | 51.41 | 5.93 | 8.79 | 3.56 |

EXAMPLE 9

(2S,3aS,7aS)-1-[(2S)-2-{[(1S)-1-(Ethoxycarbonyl)-butyl]-amino}-propionyl]-octahydro-1H-indole-2-carboxylic acid-{2-[(3-{[5-oxido-4-(phenylsulphonyl)-1,2,5-oxadiazol-3-yl]-oxy}-propionyl)-amino]-ethyl}-phosphonic acid (1:1)

Step A: {[(3-{[5-Oxido-4-(phenylsulphonyl)-1,2,5-oxadiazol-3-yl]-oxy}-propionyl)-amino]-ethyl}-phosphonic acid (Compound $B_7$)

The compound is obtained according to the procedure described in Step A of Example 7, with the replacement of aminomethylphosphonic acid with aminoethylphosphonic acid.

Melting point: 162° C.

Step B: (2S,3aS,7aS)-1-[(2S)-2-{[(1S)-1-(Ethoxycarbonyl)-butyl]-amino}-propionyl]-octahydro-1H-indole-2-carboxylic acid-{2-[(3-{[5-oxido-4-(phenylsulphonyl)-1,2,5-oxadiazol-3-yl]-oxy}-propionyl)-amino]-ethyl}-phosphonic acid (1:1)

The compound is obtained according to the procedure described in Step E of Example 1, starting from perindopril and the compound obtained in the above Step.

Elemental microanalysis:

|  | % C | % H | % N | % S |
|---|---|---|---|---|
| Calculated | 48.66 | 6.13 | 8.87 | 4.06 |
| Found | 48.81 | 6.06 | 8.90 | 4.42 |

EXAMPLE 10

(2S,3aS,7aS)-1-[(2S)-2-{[(1S)-1-(Ethoxycarbonyl)-butyl]-amino}-propionyl]-octahydro-1H-indole-2-carboxylic acid-(2-{[5-oxido-4-(phenylsulphonyl)-1,2,5-oxadiazol-3-yl]-oxy}-ethyl)-phosphonic acid (1:1)

Step A: Dimethyl (2-{[5-oxido-4-(phenylsulphonyl)-1,2,5-oxadiazol-3-yl]-oxy}-ethyl phosphonate 50% NaOH solution in water (1.5 g-32 mmol) is added in the course of ½ hour to a solution of 3,4-bis(phenylsulphonyl)-1,2,5-oxadiazole 2-oxide (7.5 g-20.7 mmol) and dimethyl 2-hydroxyethylphosphonate (4.5 g-31 mmol) in 100 ml of THF. After stirring for 1 hour, the solvent is removed in vacuo and the residue is taken up in water (100 ml) and ethyl acetate (100 ml). The organic phases is dried over $Na_2SO_4$ and then evaporated to dryness. The residue is purified by flash chromatography using a (95/5) dichloromethane/ethanol mixture as eluant to yield the expected product in the form of a colourless oil.

Step B: (2-{[5-Oxido-4-(phenylsulphonyl)-1,2,5-oxadiazol-3-yl]-oxy}-ethyl)-phosphonic acid (Compound $B_{10}$)

2.9 ml of trimethylsilyl bromide (4 eq.) are added to a solution of the compound obtained in the above Step (1.8 g-4 mmol) in 50 ml of dioxane, and then the reaction mixture is heated for 4 hours at 60° C.

The solvents are evaporated off to dryness. The residue is purified on a Biogel column eluted with a (1/1) water/acetonitrile mixture. The fractions containing the pure product are lyophilised.

Step C: (2S,3aS,7aS)-1-[(2S)-2-{[(1S)-1-(Ethoxycarbonyl)-butyl]-amino}-propionyl]-octahydro-1H-indole-2-carboxylic acid-(2-{[5-oxido-4-(phenylsulphonyl)-1,2,5-oxadiazol-3-yl]-oxy}-ethyl)-phosphonic acid (1:1)

The compound is obtained according to the procedure described in Step E of Example 1, starting from perindopril and the compound obtained in the above Step.

Elemental microanalysis:

|  | % C | % H | % N | % S |
|---|---|---|---|---|
| Calculated | 48.46 | 6.03 | 7.80 | 4.46 |
| Found | 48.53 | 5.97 | 7.95 | 4.61 |

EXAMPLE 11

(2S,3aS,7aS)-1-[(2S)-2-{[(1S)-1-(ethoxycarbonyl)-butyl]-amino}-propionyl]-octahydro-1H-indole-2-carboxylic acid-mono-(6-nitrooxy-hexahydro-furo[3,2-b]furan-3-yl)succinate (1:1)

Step A: Mono-(6-nitrooxy-hexahydro-furo[3,2-b]furan-3-yl succinate (Compound $B_{12}$)

A solution of isosorbide mononitrate (5.73 g-30 mmol), succinic anhydride (3.0 g-30 mmol) and 100 mg of DMAP in 100 ml acetonitrile is heated at reflux for 20 hours.

The solvent is then removed by evaporation. The product is purified by flash chromatography using a (98/2) dichloromethane/ethanol mixture as eluant.

The product obtained is re-crystallised from diisopropyl ether to yield the expected product in the form of a white solid.

Melting point: 65° C.

Step B: (2S,3aS,7aS)-1-[(2S)-2-{[(1S)-1-(Ethoxycarbonyl)-butyl]-amino}-propionyl]-octahydro-1H-indole-2-carboxylic acid-mono-(6-nitrooxy-hexahydro-furo[3,2-b]furan-3-yl) succinate (1:1)

The compound is obtained according to the procedure described in Step E of Example 1, starting from perindopril and the compound obtained in the above Step.

Elemental microanalysis:

|  | % C | % H | % N |
|---|---|---|---|
| Calculated | 52.80 | 6.88 | 6.37 |
| Found | 52.66 | 6.87 | 6.65 |

EXAMPLE 12

(2S,3aS,7aS)-1-[(2S)-2-{[(1S)-1-(Ethoxycarbonyl)-butyl]-amino}-propionyl]-octahydro-1H-indole-2-carboxylic acid-N-(3-{[5-oxido-4-(phenylsulphonyl-1,2,5-oxadiazol-3-yl]-oxy}-propionyl)-glycine acid (1:1)

Step A: tert-Butyl N-(3-{[5-oxido-4-(phenysulphonyl-1,2,5-oxadiazol-3-yl]-oxy}-propionyl)-glycinate A solution of the compound obtained in Step B of Example 1 (1.5 g-4 mmol), tert-butyl glycinate (0.6 g-4 mmol), EDCI (0.81 g-4 mmol) and HOBT (0.57 g-4 mmol) in 100 ml of anhydrous DMF is stirred for 24 hours at ambient temperature under argon. The DMF is then removed by distillation and the residue is taken up in 100 ml of water and 100 ml of ethyl acetate. The organic phase is washed with 5% $NaHCO_3$ solution in water, dried over $Na_2SO_4$ and then evaporated to dryness. Purification by flash chromatography is carried out using a (95/5) dichloromethane/ethyl acetate mixture as eluant to yield the expected product in the form of a colourless oil.

Step B: N-(3-{[5-Oxido-4-(phenylsulphonyl-1,2,5-oxadiazol-3-yl]-oxy}-propionyl)-glycine acid (Compound $B_{13}$)

A solution of the compound obtained in the above Step (1.7 g-4 mmol) in 100 ml of dichloromethane and 10 ml of TFA is stirred for 6 hours at ambient temperature.
The solvents are then removed in vacuo and the residue is triturated in diethyl ether for 2 hours until crystallisation occurs. Filter off with suction, dry under a pump vacuum.
Melting point: 177° C.

Step C: (2S,3aS,7aS)-1-[(2S)-2-{[(1S)-1-(Ethoxycarbonyl)-butyl]-amino}-propionyl]-octahydro-1H-indole-2-carboxylic acid-N-(3-{[5-oxido-4-(phenyl-sulphonyl-1,2,5-oxadiazol-3-yl]-oxy}-propionyl)-glycine acid (1:1)

The compound is obtained according to the procedure described in Step E of Example 1, starting from perindopril and the compound obtained in the above Step.

EXAMPLE 13

(2S)-2-[(4-{[5-Oxido-4-(phenylsulphonyl)-1,2,5-oxadiazol-3-yl]-oxy}-butanoyl)-amino]-succinic acid-(2S,3aS,7aS)-1-[(2S)-2-{[(1S)-1-(ethoxycarbo-nyl)-butyl]-amino}-propionyl]-octahydro-1H-indole-2-carboxylic acid (1:1)

Step A: 4-[(5-Oxido-4-(phenylsulphonyl)-1,2,5-oxa-diazol-3-yl)-oxy]-butanoic acid (Compound $B_{16}$)

The expected compound is obtained according to the procedure described in Steps A and B of Example 1, with the replacement of tert-butyl 3-hydroxypropionate with tert-butyl 4-hydroxybutanoate in Step A.
Melting point: 130-131° C.

Step B: (2S)-2-[(4-{[5-Oxido-4-(phenylsulphonyl)-1,2,5-oxadiazol-3-yl]-oxy}-butanoyl)-amino]-succinic acid (Compound $B_{14}$)

The expected compound is obtained according to the procedure described in Steps C and D of Example 1, starting from the compound obtained in the above Step.

Step C: (2S)-2-[(4-{[5-Oxido-4-(phenylsulphonyl)-1,2,5-oxadiazol-3-yl]-oxy}-butanoyl)-amino]-succinic acid-(2S,3aS,7aS)-1-[(2S)-2-{[(1S)-1-(ethoxycarbo-nyl)-butyl]-amino}-propionyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N | % S |
|---|---|---|---|---|
| Calculated | 51.78 | 6.08 | 8.63 | 3.95 |
| Found | 52.52 | 6.05 | 8.82 | 3.47 |

EXAMPLE 14

{[5-Oxido-4-(phenylsulphonyl)-1,2,5-oxadiazol-3-yl]-oxy}-acetic acid-(2S,3aS,7aS)-1-[(2S)-2-{[(1S)-1-(ethoxycarbonyl)-butyl]-amino}-propionyl]-oc-tahydro-1H-indole-2-carboxylic acid (1:1)

Step A: {[5-Oxido-4-(phenylsulphonyl)-1,2,5-oxa-diazol-3-yl]oxy}acetic acid (Compound $B_{15}$)

The expected compound is obtained according to the procedure described in Steps A and B of Example 1, with the replacement of tert-butyl 3-hydroxypropionate with tert-butyl hydroxyacetate in Step A.

Step B: {[5-Oxido-4-(phenylsulphonyl)-1,2,5-oxa-diazol-3-yl]-oxy}-acetic acid-(2S,3aS,7aS)-1-[(2S)-2-{[(1S)-1-(ethoxycarbonyl)-butyl]-amino}-propio-nyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N | % S |
|---|---|---|---|---|
| Calculated | 52.09 | 6.03 | 8.38 | 4.80 |
| Found | 51.76 | 5.84 | 8.50 | 4.97 |

EXAMPLE 15

3-[(5-Oxido-4-(phenylsulphonyl)-1,2,5-oxadiazol-3-yl)-oxy]-propionic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in Step B of Example 1.

EXAMPLE 16

4-[(5-Oxido-4-(phenylsulphonyl)-1,2,5-oxadiazol-3-yl)-oxy]-butanoic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in Step A of Example 13.

EXAMPLE 17

3-({4-[(4-Chlorophenyl)sulphonyl]-5-oxido-1,2,5-oxadiazol-3-yl}oxy)-propionic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: 3-({4-[(4-Chlorophenyl)sulphonyl]-5-oxido-1,2,5-oxadiazol-3-yl}oxy)-propionic acid (Compound $B_{17}$)

The expected compound is obtained according to the procedure described in Steps A and B of Example 1, with the replacement of 3,4-bis(phenylsulphonyl)-1,2,5-oxadiazole 2-oxide with 3,4-bis[(4-chlorophenyl)-sulphonyl]-1,2,5-oxadiazole 2-oxide in Step A.

Step B: 3-({4-[(4-Chlorophenyl)sulphonyl]-5-oxido-1,2,5-oxadiazol-3-yl}oxy)-propionic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

EXAMPLE 18

(2S)-2-{[3-({4-[(4-Chlorophenyl)sulphonyl]-5-oxido-1,2,5-oxadiazol-3-yl}oxy)propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: (2S)-2-{[3-({4-[(4-Chlorophenyl)sulphonyl]-5-oxido-1,2,5-oxadiazol-3-yl}oxy)propionyl]amino}succinic acid (Compound $B_{18}$)

The expected compound is obtained according to the procedure described in Steps C and D of Example 1, starting from the compound obtained in Step A of Example 17.

Step B: (2S)-2-{[3-({4-[(4-Chlorophenyl)sulphonyl]-5-oxido-1,2,5-oxadiazol-3-yl}oxy)propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N | % S | % Cl |
|---|---|---|---|---|---|
| Calculated | 49.07 | 5.57 | 8.41 | 3.85 | 4.26 |
| Found | 49.12 | 5.82 | 8.27 | 3.70 | 4.12 |

EXAMPLE 19

(2S)-2-[(3-{[5-Oxido-4-(phenylsulphonyl)-1,2,5-oxadiazol-3-yl]-oxy}-acetyl)-amino]-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: (2S)-2-[(3-{[5-Oxido-4-(phenylsulphonyl)-1,2,5-oxadiazol-3-yl]-oxy}-acetyl)-amino]-succinic acid (Compound $B_{24}$)

The expected compound is obtained according to the procedure described in Steps A to D of Example 1, with the replacement of tert-butyl 3-hydroxypropionate with tert-butyl hydroxyacetate in Step A.

Step B: (2S)-2-[(3-{[5-Oxido-4-(phenylsulphonyl)-1,2,5-oxadiazol-3-yl]-oxy}-acetyl)-amino]-succinic acid-(2S,3aS,7aS)-1-[(2S)-2-{[1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.
Elemental microanalysis:

|  | % C | % H | % N | % S |
|---|---|---|---|---|
| Calculated | 50.57 | 5.79 | 8.94 | 4.09 |
| Found | 50.71 | 5.79 | 9.04 | 3.82 |

EXAMPLE 20

(2S)-2-[(2-{[5-Oxido-4-(phenylsulphonyl)-1,2,5-oxadiazol-3-yl]oxy}ethyl)amino]succinic acid:(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: Di-tert-butyl (2S)-2-[(2-hydroxyethyl)amino]succinate

A solution of di-tert-butyl L-aspartate (5.62 g-20 mmol), 2-bromoethanol (2.84 ml-40 mmol) and $K_2CO_3$ (5.6 g-40 mmol) in 100 ml of acetonitrile is heated at reflux for 16 hours. The mineral salts are filtered off and the solvent is removed by distillation in vacuo. The crude product so obtained is purified by flash chromatography on silica gel using a (95/5) dichloromethane/ethanol mixture as eluant. The expected product is obtained in the form of a colourless oil.

Step B: (2S)-2-[(2-{[5-Oxido-4-(phenylsulphonyl)-1,2,5-oxadiazol-3-yl]oxy}ethyl)amino]succinic acid (Compound $B_{25}$)

The compound is obtained according to the procedure described in Steps A and B of Example 1, with the replacement of tert-butyl 3-hydroxypropionate with the compound obtained in the above Step.

Melting point: 160-161° C.

Step C: (2S)-2-[(2-{[5-Oxido-4-(phenylsulphonyl)-1,2,5-oxadiazol-3-yl]oxy}ethyl)amino]succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Elemental microanalysis:

|  | % C | % H | % N | % S |
|---|---|---|---|---|
| Calculated | 51.49 | 6.15 | 9.10 | 4.17 |
| Found | 51.05 | 5.94 | 9.20 | 4.06 |

EXAMPLE 21

(2S)-2-{[3-({4-[(4-Methylphenyl)sulphonyl]-5-oxido-1,2,5-oxadiazol-3-yl}oxy)propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: (2S)-2-{[3-({4-[(4-Methylphenyl)sulphonyl]-5-oxido-1,2,5-oxadiazol-3-yl}oxy)propionyl]amino}succinic acid (Compound $B_{21}$)

The compound is obtained according to the procedure described in Steps A to D of Example 1, with the replacement of 3,4-bis(phenylsulphonyl)-1,2,5-oxadiazole 2-oxide with 3,4-bis[(4-methylphenyl)sulphonyl]-1,2,5-oxadiazole 2-oxide in Step A.

Melting point: 167-168° C.

Step B: (2S)-2-{[3-({4-[(4-Methylphenyl)sulphonyl]-5-oxido-1,2,5-oxadiazol-3-yl}oxy)propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Elemental microanalysis:

|  | % C | % H | % N | % S |
|---|---|---|---|---|
| Calculated | 51.78 | 6.08 | 8.63 | 3.95 |
| Found | 51.92 | 5.96 | 8.45 | 3.96 |

EXAMPLE 22

(2S)-2-{[3-({4-[(4-Chlorophenyl)sulphonyl]-5-oxido-1,2,5-oxadiazol-3-yl}oxy)butanoyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: (2S)-2-{[3-({4-[(4-Chlorophenyl)sulphonyl]-5-oxido-1,2,5-oxadiazol-3-yl}oxy)butanoyl]amino}succinic acid (Compound $B_{26}$)

The expected compound is obtained according to the procedure described in Steps A to D of Example 1 with the replacement, in Step A, of tert-butyl 3-hydroxypropionate with tert-butyl 4-hydroxybutanoate, and of 3,4-bis(phenylsulphonyl)-1,2,5-oxadiazole 2-oxide with 3,4-bis[(4-chlorophenyl)-sulphonyl]-1,2,5-oxadiazole 2-oxide.

Melting point: 145-146° C.

Step B: (2S)-2-{[3-({4-[(4-Chlorophenyl)sulphonyl]-5-oxido-1,2,5-oxadiazol-3-yl}oxy)butanoyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Elemental microanalysis:

|  | % C | % H | % N | % S | % Cl |
|---|---|---|---|---|---|
| Calculated | 49.67 | 5.72 | 8.28 | 3.79 | 4.19 |
| Found | 49.44 | 5.78 | 8.20 | 3.70 | 4.10 |

EXAMPLE 23

(2S)-2-{[3-({4-[(4-Methylphenyl)sulphonyl]-5-oxido-1,2,5-oxadiazol-3-yl}oxy)butanoyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: (2S)-2-{[3-({4-[(4-Methylphenyl)sulphonyl]-5-oxido-1,2,5-oxadiazol-3-yl}oxy)butanoyl]amino}succinic acid (Compound $B_{27}$)

The expected compound is obtained according to the procedure described in Steps A to D of Example 1 with the replacement, in Step A, of tert-butyl 3-hydroxypropionate with tert-butyl 4-hydroxybutanoate, and of 3,4-bis(phenylsulphonyl)-1,2,5-oxadiazole 2-oxide with 3,4-bis[(4-methylphenyl)-sulphonyl]-1,2,5-oxadiazole 2-oxide.

Melting point: 147-148° C.

Step B: (2S)-2-{[3-({4-[(4-Methylphenyl)sulphonyl]-5-oxido-1,2,5-oxadiazol-3-yl}oxy)butanoyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Elemental microanalysis:

|  | % C | % H | % N | % S |
| --- | --- | --- | --- | --- |
| Calculated | 52.36 | 6.22 | 8.48 | 3.88 |
| Found | 52.66 | 6.15 | 8.67 | 4.16 |

EXAMPLE 24

2-[(3-{[5-Oxido-4-(phenylsulphonyl)-1,2,5-oxadiazol-3-yl]-oxy}-butanoyl)-amino]-ethanesulphonic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: 2-[(3-{[5-Oxido-4-(phenylsulphonyl)-1,2,5-oxadiazol-3-yl]-oxy}-butanoyl)-amino]-ethanesulphonic acid (Compound $B_{28}$)

The expected compound is obtained according to the procedure described in Steps A and B of Example 6 with the replacement, in Step A, of compound $B_4$ with compound $B_{16}$ obtained in Step A of Example 13.

Melting point: 131-132° C.

Step B: 2-[(3-{[5-Oxido-4-(phenylsulphonyl)-1,2,5-oxadiazol-3-yl]-oxy}-butanoyl)-amino]-ethanesulphonic acid-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Elemental microanalysis:

|  | % C | % H | % N | % S |
| --- | --- | --- | --- | --- |
| Calculated | 49.30 | 6.14 | 8.71 | 7.98 |
| Found | 49.15 | 6.12 | 8.82 | 8.22 |

EXAMPLE 25

N,N-Bis(2-sulphoethyl)-4-{[5-oxido-4-(phenylsulphonyl)-1,2,5-oxadiazol-3-yl]oxy}butanamide-(2S,3aS,7aS)-1-[(2S)-2-{[(1S)-1-(ethoxycarbonyl)-butyl]-amino}-propionyl]-octahydro-1H-indole-2-carboxylic acid (1:1)

Step A: N-{2-[(3-{[5-Oxido-4-(phenylsulphonyl)-1,2,5-oxadiazol-3-yl]-oxy}-butanoyl)-oxy]}-5-norbornene-2,3-dicarboximide The expected compound is obtained according to the procedure described in Step A of Example 6, with the replacement of compound $B_4$ with compound $B_{16}$ obtained in Step A of Example 13.

Step B: N,N-Bis(2-sulphoethyl)-4-{[5-oxido-4-(phenylsulphonyl)-1,2,5-oxadiazol-3-yl]oxy}butanamide (Compound $B_{29}$)

The expected compound is obtained according to the procedure described in Step B of Example 6, starting from ditaurine (prepared according to DE 10033580) and the compound obtained in the above Step.

Step C: N,N-Bis(2-sulphoethyl)-4-{[5-oxido-4-(phenylsulphonyl)-1,2,5-oxadiazol-3-yl]oxy}butanamide-(2S,3aS,7aS)-1-[(2S)-2-{[(1S)-1-(ethoxycarbonyl)-butyl]-amino}-propionyl]-octahydro-1H-indole-2-carboxylic acid (1:1)

The compound is obtained according to the procedure described in Step E of Example 1, starting from perindopril and the compound obtained in the above Step.

Pharmacological Study of the Products of the Invention

EXAMPLE 26

NO Donor Activity

In Vitro

Aorta rings without endothelium are used. After a first contraction induced by 60 mM KCl to characterise the sensitivity of the ring, and washing, a stable contraction is induced by noradrenaline (0.1-0.3 μM) in the presence or absence of a guanylate cyclase inhibitor, ODQ (10 μM). A cumulative concentration series is applied and the activity of the product under test is calculated by an $IC_{50}$ (dose that inhibits the maximum effect by 50%).

Results: the compounds according to the invention have a quite significant relaxing effect; by way of example, the compounds of Examples 1 and 7 have $IC_{50}$ values of 0.048 and 0.047 μM, respectively.

EXAMPLE 27

Activity Inhibiting Angiotensin 1-Converting Enzyme

In Vivo

Rats are anaesthetised with pentobarbital and placed under artificial respiration, and the average arterial pressure is measured by a catheter that has been placed in the femoral artery and is connected to a pressure sensor. The vagus nerves are divided into sections and mecamilamine (sympathetic ganglion blocker) is injected i.v. at 1.5 mg/kg. After stabilisation, angiotensin I is injected i.v. at 1.5 µg/kg.

The maximum hypertensive response to angiotensin I is measured in rats that, 60 minutes prior to anaesthesia, have received by the oral route either Senegal gum alone (control group), or the compound under test in Senegal gum. The inhibitory effect is determined as a percentage from the response to angiotensin I compared with the control group.

Results: the compounds according to the invention have a quite significant inhibitory effect;
by way of example, injected at a dose of 0.1 mg/kg the compounds of Examples 1 and 7 result in angiotensin I inhibitions of 85 and 88% respectively.

EXAMPLE 28

Pharmaceutical Composition

Preparation formula for 1000 tablets each containing a dose of 100 mg

| | |
|---|---|
| Compound of one of Examples 1 to 25 | 100 g |
| Hydroxypropyl cellulose | 2 g |
| Wheat starch | 10 g |
| Lactose | 100 g |
| Magnesium stearate | 3 g |
| Talc | 3 g |

The invention claimed is:

1. A compound selected from those of formula (I):

$$(A)_m \cdot (B)_n \qquad (I)$$

wherein A represents

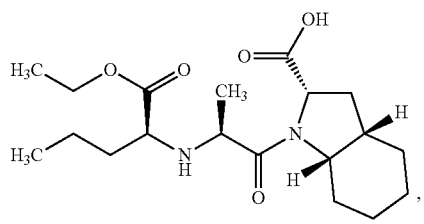

B represents a compound selected from those of formula (III):

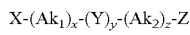

$$X\text{-}(Ak_1)_x\text{-}(Y)_y\text{-}(Ak_2)_z\text{-}Z \qquad (III)$$

wherein:
X represents a $CO_2H$, $SO_3H$ or $P(O)(OH)_2$ group,
$Ak_1$ and $Ak_2$, which may be identical or different, each represents a saturated or unsaturated, linear or branched $C_1$-$C_8$ alkylene group in which one or more of the carbon atoms may be replaced by an oxygen, sulphur or nitrogen atom or by an $SO_2$ group, and wherein the alkylene group is optionally substituted by one or more groups selected from $CO_2H$, $SO_3H$, hydroxy and amino,
x, y and z, which may be identical or different, each represents 0 or 1,
Y represents CO or CONH, and
Z represents an NO donor group, m represents the number of acid functions of B that have been converted to a salt and n represents the number of basic functions of A that have been converted to a salt, and wherein
the bond or bonds between A and B are of the ionic type.

2. The compound of claim 1, wherein the compound of formula (III) is selected from:

(IIIa)

(IIIb)

(IIIc)

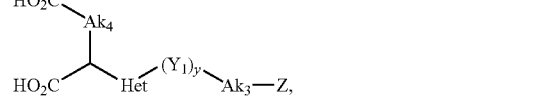

(IIId)

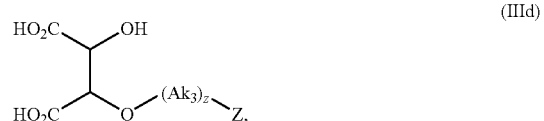

(IIIe)

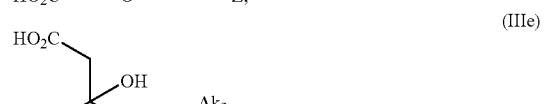

(IIIf)

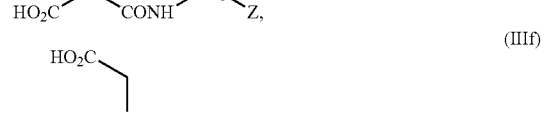

(IIIg)

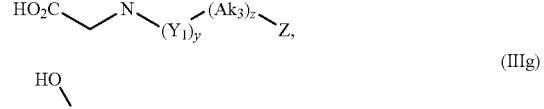

(IIIh)

(IIIi)

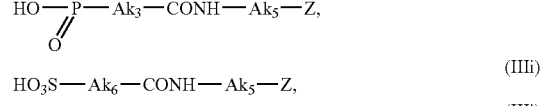

(IIIj)

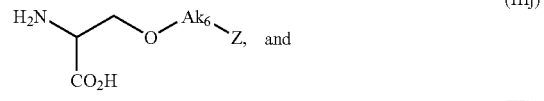

and (IIIk)

wherein:
$Ak_1$ represents a saturated or unsaturated, linear or branched $C_1$-$C_8$ alkylene group in which one or more of the carbon atoms may be replaced by an oxygen, sulphur or nitrogen atom or by an $SO_2$ group, and wherein the alkylene group is optionally substituted by one or more groups selected from $CO_2H$, $SO_3H$, hydroxy and amino,
x, y and z, which may be identical or different, each represents 0 or 1,
Y represents CO or CONH,
Z represents an NO donor group,
$Ak_3$ and $Ak_5$, which may be identical or different, each represents a saturated linear or branched $C_1$-$C_6$ alkylene group in which one or more of the carbon atoms may be replaced by an oxygen, sulphur or nitrogen atom or by an SO$_2$ group, Ak$_4$ represents a saturated linear or branched C$_1$-C$_3$alkylene group in which one of the carbon atoms may be replaced by an oxygen, sulphur or nitrogen atom or by an SO$_2$ group, Ak$_6$ represents a saturated linear or branched C$_2$-C$_5$alkylene group in which one of the carbon atoms may be replaced by an oxygen, sulphur or nitrogen atom or by an SO$_2$ group, Het represents O or NH, and Y$_1$ represents a carbonyl group.

3. The compound of claim 1, wherein Z is selected from:

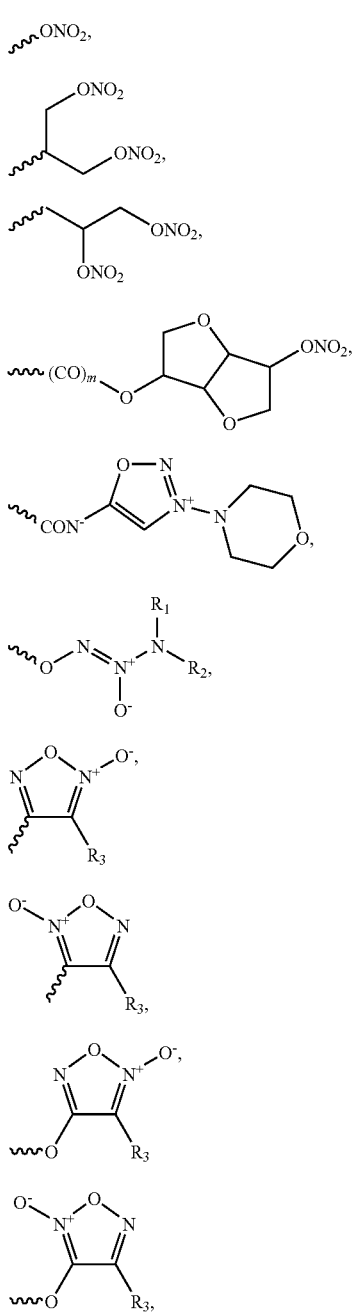

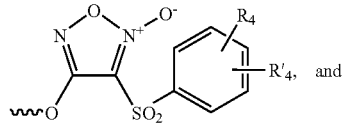

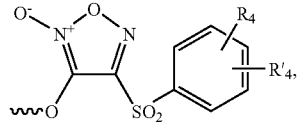

wherein:

m represents 0 or 1,

R$_1$ and R$_2$, which may be identical or different, each represents a linear or branched C$_1$-C$_6$alkyl group, or R$_1$ and R$_2$, together with the nitrogen atom carrying them, form a nitrogen-containing heterocycle having from 3 to 7 ring members which is optionally substituted by a linear or branched C$_1$-C$_6$alkyl group, R$_3$ represents a methyl or aminocarbonyl group, and R$_4$ and R'$_4$, which may be identical or different, each represents a hydrogen or halogen atom or a linear or branched C$_1$-C$_6$alkyl, trifluoromethyl or trifluoromethoxy group.

4. The compound of claim 1, wherein B represents a compound selected from:

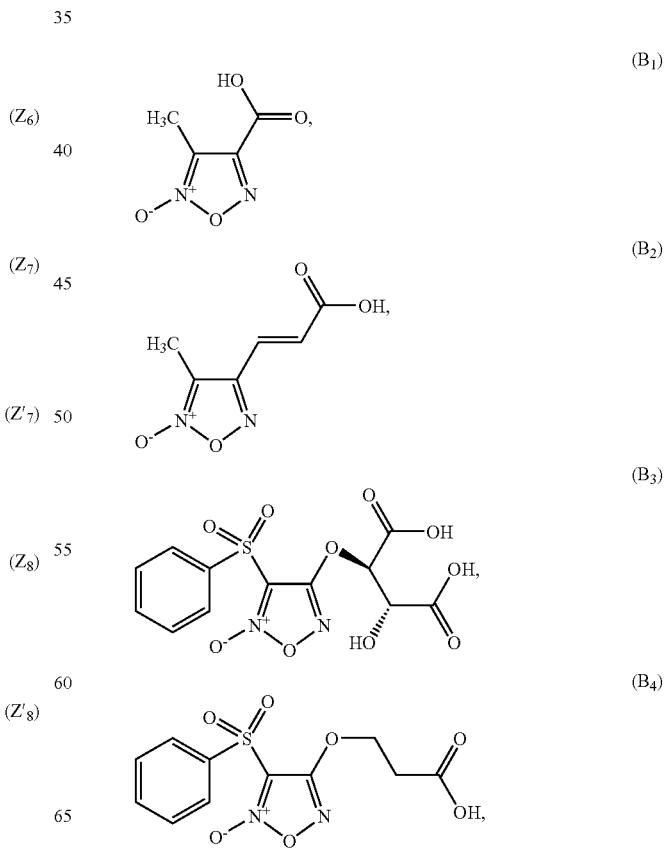

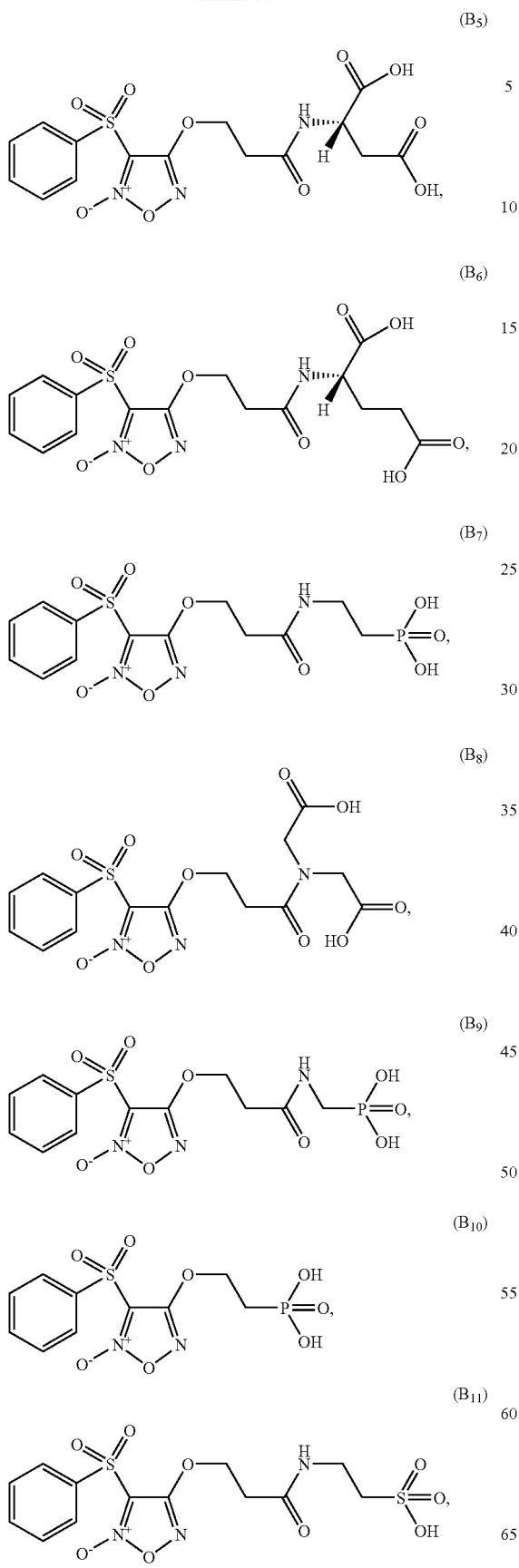
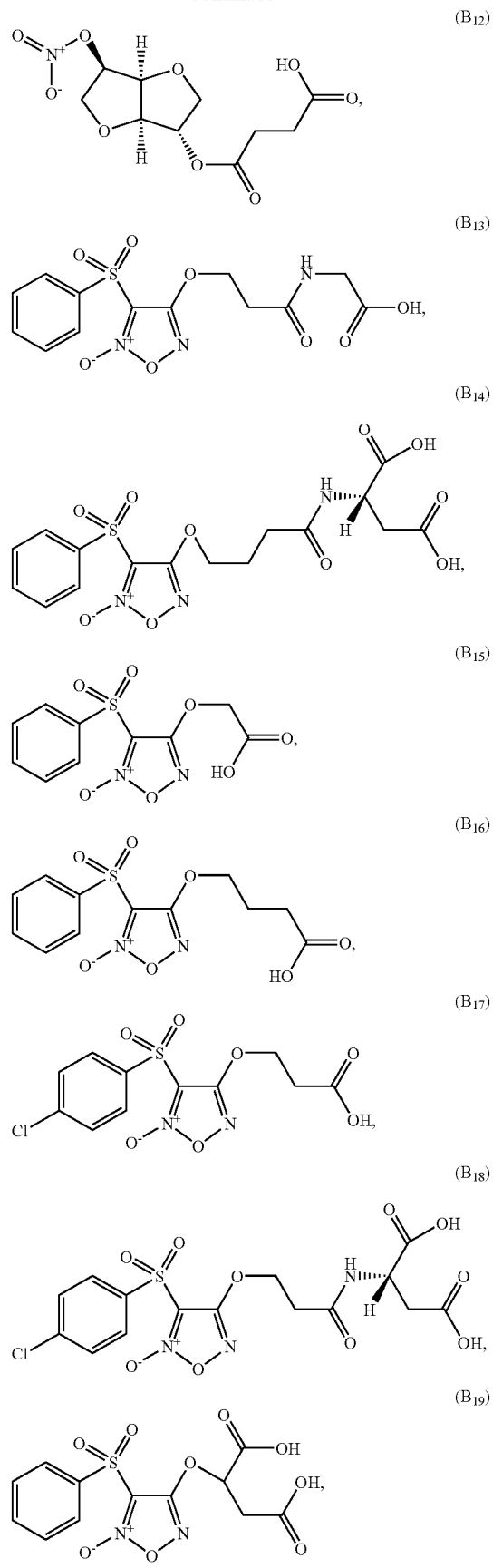

(B20) 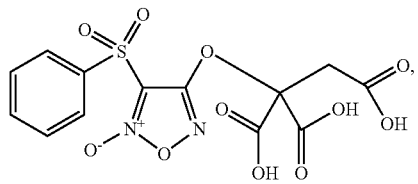

(B21) 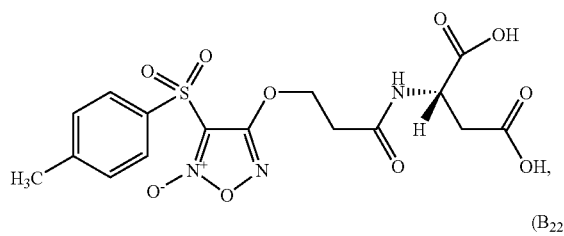

(B22) 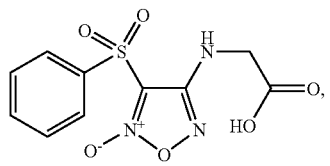

(B23) 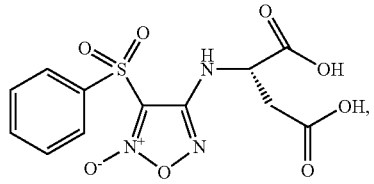

(B24) 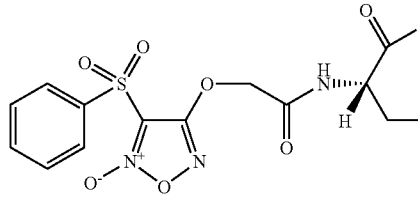

(B25) 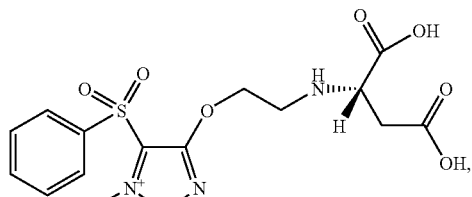

(B26) 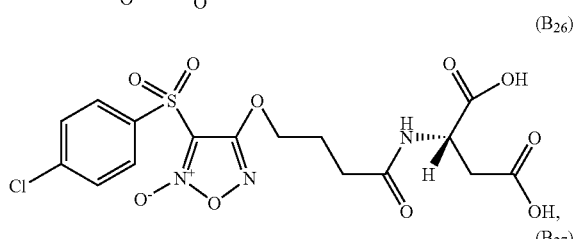

(B27) 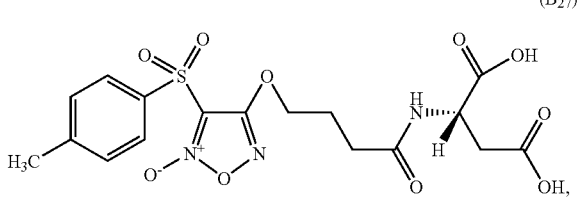

(B28) 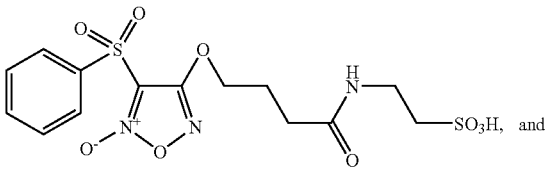

(B29) 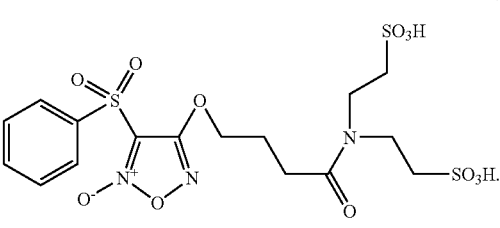

5. The compound of claim 1, which is selected from:

(2S)-2-[(3-{[5-oxido-4-(phenylsulphonyl)-1,2,5-oxadiazol-3-yl]-oxy}-propionyl)-amino]-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S)-2-[(3-{[5-oxido-4-(phenylsulphonyl)-1,2,5-oxadiazol-3-yl]-oxy}-propionyl)-amino]-pentanedioic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

2-[(3-{[5-oxido-4-(phenylsulphonyl)-1,2,5-oxadiazol-3-yl]-oxy}-propionyl)-amino]-ethanesulphonic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-{[(3-{[5-oxido-4-(phenylsulphonyl)-1,2,5-oxadiazol-3-yl]-oxy}-propionyl)-amino]-methyl}-phosphonic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-2,2'-[(3-{[5-oxido-4-(phenylsulphonyl)-1,2,5-oxadiazol-3-yl]-oxy}-propionyl)-imino]-diacetic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-{2-[(3-{[5-oxido-4-(phenylsulphonyl)-1,2,5-oxadiazol-3-yl]-oxy}-propionyl)-amino]-ethyl}-phosphonic acid (1:1);

(2S,3aS,7aS)-1-[(2S)-2-{[(1S)-1-(ethoxycarbonyl)-butyl]-amino}-propionyl]-octahydro-1H-indole-2-carboxylic acid-(2-{[5-oxido-4-(phenylsulphonyl)-1,2,5-oxadiazol-3-yl]-oxy}-ethyl)-phosphonic acid (1:1);

(2S)-2-[(4-{[5-oxido-4-(phenylsulphonyl)-1,2,5-oxadiazol-3-yl]-oxy}-butanoyl)-amino]-succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S)-2-{[3-({4-[(4-chlorophenyl)sulphonyl]-5-oxido-1,2,5-oxadiazol-3-yl}oxy)propionyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1);

(2S)-2-{[3-({4-[(4-methylphenyl)sulphonyl]-5-oxido-1,2,5-oxadiazol-3-yl}oxy)propionyl]amino}succinic acid-(2S,3aS,7aS)-1-[(2S)-2-{[(1S)-1-(ethoxycarbonyl)-butyl]-amino}-propionyl]octahydro-1H-indole-2-carboxylic acid (1:1); and (2S)-2-{[3-({4-[(4-methylphenyl)sulphonyl]-5-oxido-1,2,5-oxadiazol-3-yl}oxy)-butanoyl]amino}succinic acid-(2S,3aS,7aS)-1-[(2S)-2-{[(1S)-1-(ethoxycarbonyl)-butyl]-amino}-propionyl]-octahydro-1H-indole-2-carboxylic acid (1:1).

6. A pharmaceutical composition comprising as active ingredient a compound of claim 1 in combination with one or more pharmaceutically acceptable, inert, non-toxic excipients or carriers.

7. A method for treating a cardiovascular pathology selected from arterial hypertension, systolic hypertension, peripheral vascular disease, atherosclerosis, restenosis, cardiac insufficiency, thrombosis, stable or unstable angina pectoris, cerebral vascular accidents, coronary accidents, myocardial infarction, vascular remodelling, diabetes and endothelial dysfunction, comprising the step of administering to a living animal body, including a human, a therapeutically effective amount of a compound of claim 1.

* * * * *